US00PP18604P3

(12) United States Plant Patent
Olesen

(10) Patent No.: US PP18,604 P3
(45) Date of Patent: Mar. 18, 2008

(54) SHRUB ROSE PLANT NAMED 'POULTC012'

(50) Latin Name: *Rosa hybrida*
Varietal Denomination: Poultc012

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 21 days.

(21) Appl. No.: 11/389,467

(22) Filed: Mar. 23, 2006

(65) Prior Publication Data

US 2007/0226847 P1 Sep. 27, 2007

(51) Int. Cl.
*A01H 5/00* (2006.01)

(52) U.S. Cl. ..... Plt./107

(58) Field of Classification Search ..... Plt./107
See application file for complete search history.

*Primary Examiner*—Kent Bell
*Assistant Examiner*—Louanne Krawczewicz Myers

(57) ABSTRACT

A new garden rose plant of the shrub class which has abundant, pink flowers and attractive foliage. This new and distinct variety has shown to be uniform and stable in the resulting generations from asexual propagation.

2 Drawing Sheets

Botanical classification: *Rosa hybrida.*
Variety denomination: 'Poultc012'.

SUMMARY OF THE INVENTION

The present invention constitutes a new and distinct variety of garden rose plant which originated from a controlled crossing between the female seed parent, 'Pouldiram', a rose plant by the same inventor described and illustrated in U.S. Plant Pat. No. 12,568, and the male pollen parent, an unnamed seedling (non-patented). The two parents were crossed during the summer of 1996 and the resulting seeds were planted in a controlled environment in Fredensborg, Denmark. The new variety is named 'Poultc012'.

The new variety may be distinguished from the female parent, by the following combination of characteristics:

1. 'Poultc012' has growth height range of 60 to 100 cm. The seed parent reaches 150 cm of growth height.
2. The claimed plant has pink flowers while the seed parent has white flowers.

The new variety may be distinguished from its pollen parent by the following combination of characteristics:

1. The pollen parent is a low growing shrub, ranging from 40 to 60 cm in height, while the claimed plant reaches 60 to 100 cm in height.
2. The pollen parent has flowers which have fewer flower petals than the claimed plant.

The objective of the hybridization of this rose variety was to create a new and distinct variety for garden use with unique qualities, such as:

1. Uniform and abundant pink flowers;
2. Vigorous, but compact growth when propagated both as a budded rose and on its own roots;
3. Exceptional disease resistance; and
4. Dark green attractive foliage.

This combination of qualities is not present in previously available commercial cultivars of this type, known to the inventor, and distinguish 'Poultc012' from all other varieties of which we are aware.

As part of the rose development program, and Mogens N. Olesen germinated the seeds from the aforementioned hybridization during winter of 1996 and conducted evaluations on the resulting seedlings in a controlled environment in Fredensborg, Denmark.

'Poultc012' was selected in the spring 1997 by the inventor as a single plant from the progeny of the aforementioned hybridization.

Asexual reproduction of 'Poultc012' by traditional budding and rooted cuttings was first done by Mogens N. Olesen in their nursery in Fredensborg, Denmark in July, 1997. This initial and other subsequent asexual propagations conducted in controlled environments have demonstrated that the characteristics of 'Poultc012' are true to type and are transmitted from one generation to the next.

BRIEF DESCRIPTION OF THE DRAWING

The accompanying color illustrations shows as true as is reasonably possible to obtain in color photographs of this type, the typical characteristics of the buds, flowers, leaves, and stems, of 'Poultc012'. Specifically illustrated in the drawings are.

DETAILED DESCRIPTION OF THE VARIETY

Figure 1:
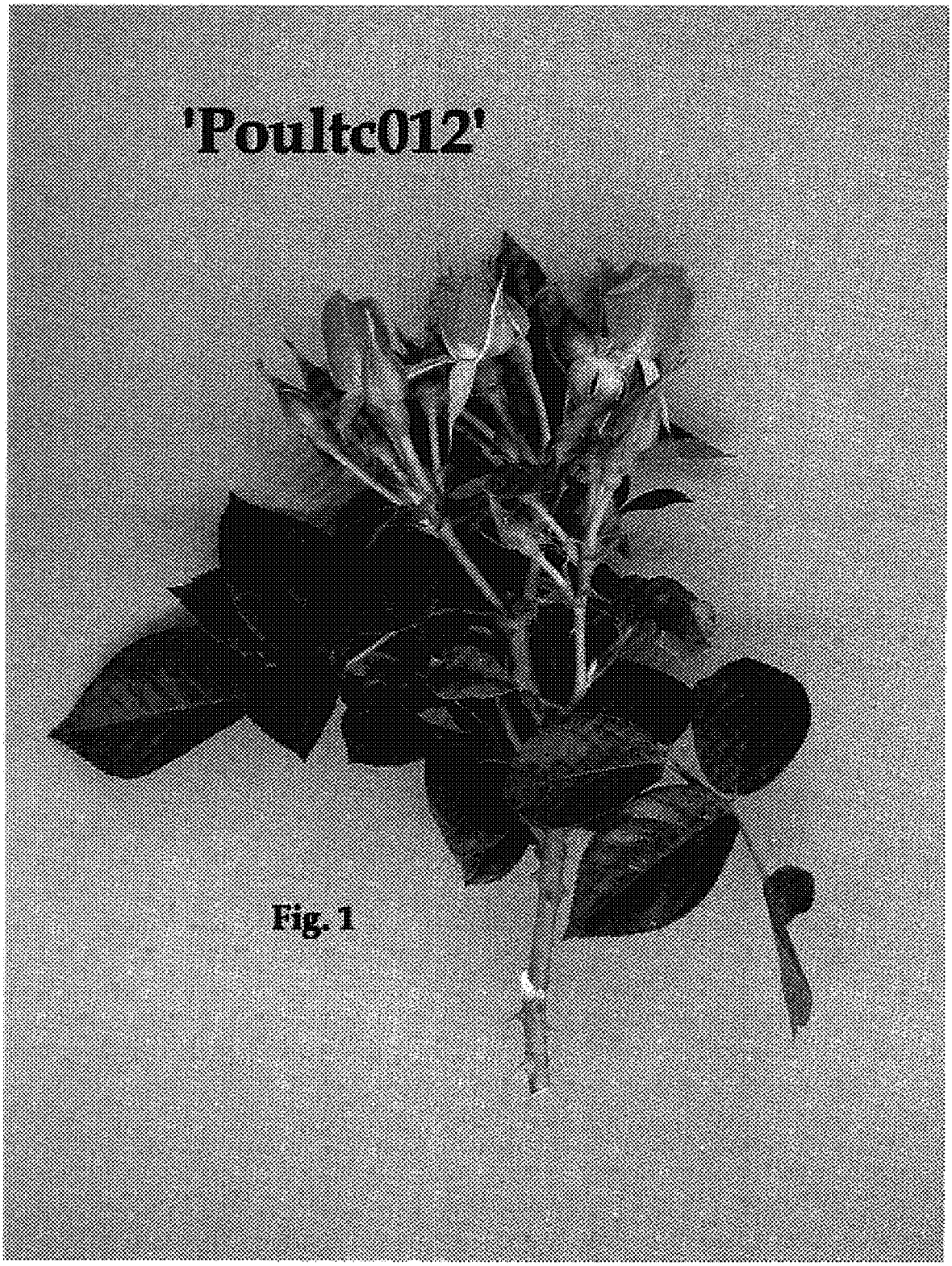
FIG. 1; Cluster of partially opened flowers and flower buds on a branch.
Figures 2A, 2B, 2C, 2D, 2E:
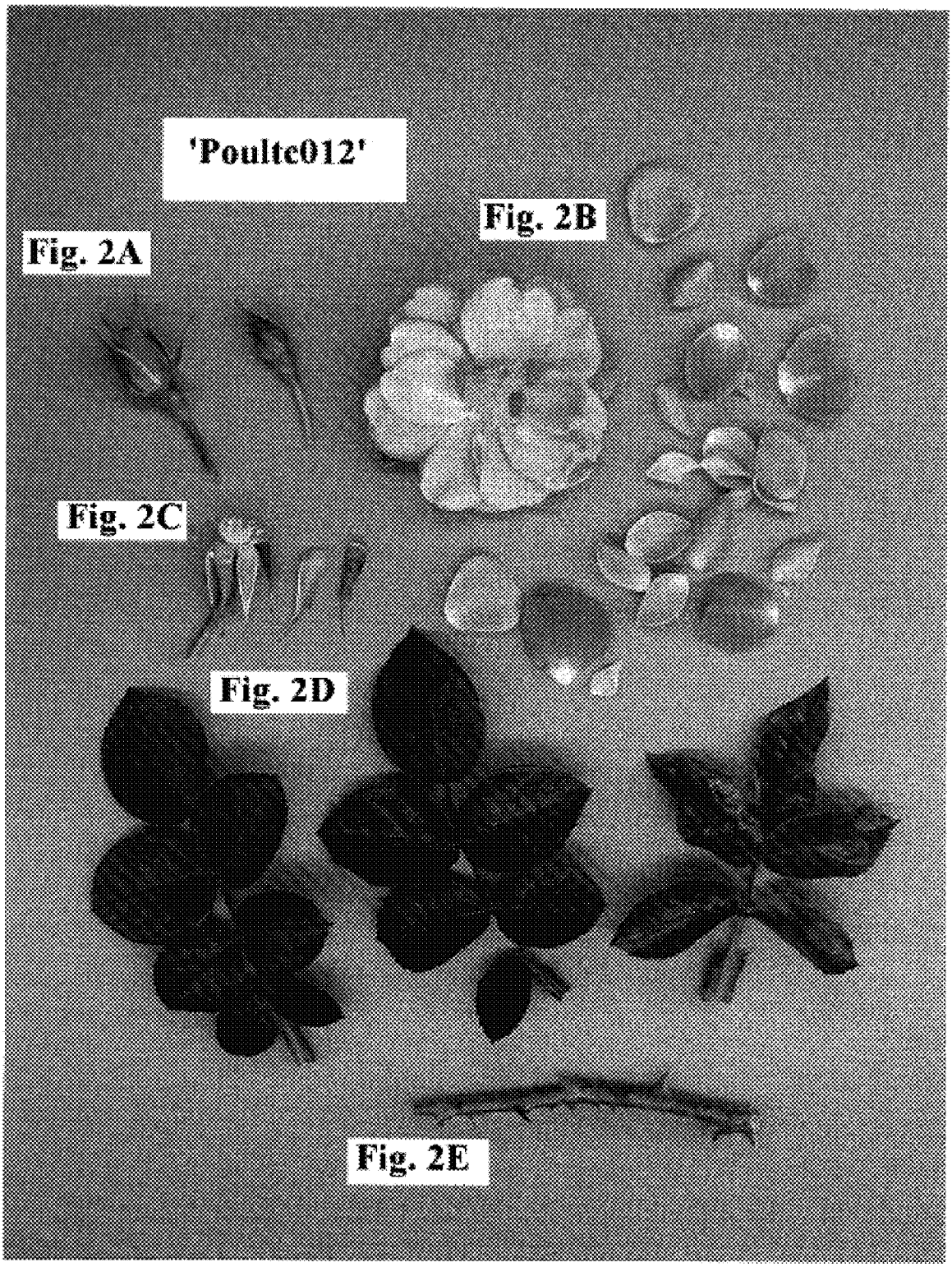
FIG. 2A; Flower bud partially opened and closed.
FIG. 2B; Open flower and flower petals, detached.
FIG. 2C; Sepals, receptacle, reproductive flower parts and peduncle.
FIG. 2D; Mature leaves and single juvenile leaf at far right.
FIG. 2E; Mature stem with thorns.

The following is a description of 'Poultc012', as observed in its growth in a field nursery in Jackson County, Oregon Observed plants are 3 years of age, grown on *Rosa multiflora* understock. Color references are made using The Royal Horticultural Society (London, England) Colour Chart, 2001, except where common terms of color are used.

For a comparison, several physical characteristics of the rose variety 'Poulalo', a rose variety from the same inventor described and illustrated in U.S. Plant Pat. No. 12,471, are compared to 'Poultc012' in Chart 1.

CHART 1

| | 'Poultc012' | 'Poulalo' |
|---|---|---|
| Flower diameter | 75 mm | 55 to 60 mm |
| Petal count | 33, with 6 to 9 petaloids | 60 to 70 petals |
| General tonality of open flower | Red-Purple Group 70D | Red-Purple Group 58C to 58D |

FLOWER AND FLOWER BUD

Blooming habit: Continuous.

Flower bud:

*Size.*—Upon opening, 25 mm in length from base of receptacle to end of bud. Diameter is 11 mm.

*Bud form.*—Ovate.

*Bud color.*—As sepals unfold, petals are Red-Purple Group 63C and Red-Purple Group 68A. Sepal Upper Surface: Color: Yellow-Green Group 147C. Surface: Medium pubescence observed. Sepal Lower Surface: Color: Yellow-Green Group 144A to 146A with Anthocyanic pigments of Greyed-Purple Group 185A. Texture: Smooth. Sepal Shape: Sepals are lanceolate. Apex is cirrhose. Base is flat at union with receptacle. Sepal Margin: Margins have weak foliaceous appendages on three of the five sepals and few stipitate glands. Size: Normally 27 mm (l)×6 mm (w).

*Receptacle.*—Surface: Smooth. Shape: Pear shaped. Size: 8 mm (h)×6 mm (w). Color: Yellow-Green Group 144A. Anthocyanic pigments the color of Greyed-Purple Group 184B observed.

*Pedicel.*—Surface: Smooth with stipitate glands. Length: 25 mm average length. Diameter: 2.5 mm on average. Color: Yellow-Green Group 144A. Anthocyanic pigments the color of Greyed-Purple Group 184B observed. Strength: Somewhat strong.

*Borne.*—In clusters or corymbs with 3 to 9 flowers per stem.

*Peduncle.*—Length is normally 10 to 30 cm. Diameter is 3.5 mm on average. There are numerous prickles on the surface, making it somewhat rough. The coloration is Yellow-Green Group 144A with light intonations of Greyed-Purple 184B.

Flower bloom:

*Fragrance.*—Light floral.

*Duration.*—The blooms have a duration on the plant of approximately 7 to 10 days. Afterwards, petals fall cleanly away from plant.

*Size.*—Flower diameter is 75 mm when open. Depth is 22 mm.

*Form.*—General shape is an open cup with petals that curve out from the center.

*Shape of flower when viewed from the side.*—Upon opening, upper part: Flattened convex. Upon opening, lower part: Flat. Open flower, upper part: Flattened convex. Open flower, lower parts: Concave.

*Petalage.*—Normally 33 petals with 6 to 9 petaloids.

Color:

*Upon opening, petals.*—Outermost petals: Outer side: Red-Purple Group 70B with soft veins the color of Red-Purple Group 65C. Inner Side: Red-Purple Group 65A at marginal zone blending with Red-Purple Group 65B at middle zone. Innermost petals: Outer side: Red-Purple Group 70C with soft veins the color of Red-Purple Group 65C. Inner Side: Red-Purple Group 65A at marginal zone blending with Red-Purple Group 65B at middle zone.

*Upon opening, basal petal spots.*—Outer side: Yellow Group 4D. Inner Side: Yellow Group 4D.

*After opening, petals.*—Outermost and innermost petals: Outer side: Red-Purple Group 70D with soft veins of Red-Purple Group 65C occurring at the middle and basal zone. Inner Side: Red-Purple Group 65B. At the basal zone there is a light overlay of White Group 155A to Yellow-Green Group 150D.

*After opening, basal petal spots.*—Outer side: White Group 155A to Yellow Group 4D. Inner Side: White Group 155A to Yellow Group 4D.

General tonality: On open flower Red-Purple Group 70D.

Petals:

*Petal reflex.*—Flat.

*Margin.*—Entire and uniform. Occasionally there is a cleft or point at center of margin.

*Shape.*—Narrow elliptical. Apex: Rounded. Base: Acute.

*Size.*—Normally 33 mm (l)×29 mm (w).

*Texture.*—Smooth.

*Thickness.*—Average.

*Arrangement.*—Not Formal.

Petaloids:

*Quantity.*—Normally 6 to 9.

*Color.*—The upper surface is Red-Purple Group 70D with a basal petal spot the color of Yellow-Green Group 150D. The lower surface is Red-Purple Group 70C with a basal petal spot the color of Yellow-Green Group 150D.

*Size.*—Normally 15 mm (l)×5 mm (w).

*Shape.*—Irregular, elliptical. asymmetric.

Reproductive organs:

*Pollen.*—Quantity: Average. Color: Yellow-Orange Group 14A.

*Anthers.*—Size: 2 mm in length. Color: Greyed-Orange Group 163A. Quantity: 90 average.

*Filaments.*—Color: Yellow-Green Group 149C. Length: Normally 5 mm.

*Pistils.*—Length: 5 mm on average. Quantity: Normally 31.

*Styles.*—Color: Yellow-Green Group 149B to 149C.

*Stigmas.*—Slightly superior in location to the length of the filaments and the height of the anthers. Color: Yellow-Green Group 145C.

*Hips.*—None Observed.

PLANT

Plant growth: Upright and bushy. When grown as a budded field grown plant on *Rosa multiflora* understock, the height of the plant is 60 to 100 cm. The average spread is 75 cm.

Stems:

*Color.*—Young wood: Yellow-Green Group 146C. Older wood: Yellow-Green Group 146A.

*Length.*—From the base of the plant to the flowering portion, normally 60 cm.

*Diameter.*—6 mm on average.

*Internodes.*—40 mm on average.

*Surface texture.*—Young wood: Rough with numerous prickles. Older wood: Rough with numerous prickles.

Prickles:

*Incidence.*—9 prickles per 10 cm of stem.

*Color.*—Juvenile prickles: Yellow-Green Group 146D and Greyed-Purple Group 185C. Mature prickles: Greyed-Yellow Group 160A.

*Shape.*—Upper side: Flat. Lower side: Concave.

*Size.*—Normally 10 mm from base to apex. 9 mm wide on average. There are various sizes of prickles ranging from 1 mm to 10 mm in height.

Plant foliage: Normal number of leaflets on normal leaves in middle of the stem: 7 leaflets.

*Compound leaf size.*—Normally 130 mm (l)×80 mm (w).

*Quantity.*—3 leaves per 10 cm of stem on average.

*Color.*—Mature Foliage: Upper surface: Yellow-Green Group 147A. Lower surface: Yellow-Green Group 146A. Juvenile Foliage: Upper surface: Yellow-Green Group 146A. Lower surface: Yellow-Green Group 146B with anthocyanic intonations the color of Greyed-Red Group 178B at margins.

Plant leaves and leaflets:

*Surface texture.*—Upper side: Smooth. Lower side: Many stipitate glands.

*Stipules.*—Size: Normally 25 to 40 mm in length. Individual stipules are 5 to 6 mm wide. Margins: Entire. Color: Yellow-Green Group 146A.

*Petiole.*—Length: Normally 28 mm. Diameter: 2 mm on average. Upper surface: Color: Yellow-Green Group 146B. Lower surface: Color: Yellow-Green Group 146B. Observations: Numerous stipitate glands and small prickles observed.

*Rachis.*—Length: 56 mm on average. Above: Color: Green Group 137A. Underneath: Color: Yellow-Green Group 146B. Observations: Numerous stipitate glands and small prickles observed.

*Leaflet.*—Size: 48 mm (l)×34 mm (w). Edge: Serrated. Shape: Generally ovate. Base: Rounded. Apex: Acuminate. Texture: Smooth. Thickness: Average. Arrangement: Odd pinnate. Venation: Reticulate. Glossiness: Very glossy.

Disease resistance: Above average resistance to powdery and downy mildew, rust, black spot, and *Botrytis* under normal growing conditions in Jackson County, Oregon Cold hardiness: The variety 'Poultc012' has been found to be cold tolerant to USDA Cold Hardiness Zone 6.

It is claimed:

1. A new and distinct variety of rose plant of the shrub rose class named 'Poultc012', substantially as illustrated and described herein, due to its abundant pink flowers, disease resistance, and extended period of bloom.

* * * * *

'Poultc012'